United States Patent [19]
Henkel

[11] Patent Number: 6,001,870
[45] Date of Patent: Dec. 14, 1999

[54] NASOPHARYNX ADMINISTRATION OF MUPIROCIN FOR PROPHYLACTIC TREATMENT OF RECURRENT OTITIS MEDIA

[75] Inventor: Timothy John Henkel, Cambridge, United Kingdom

[73] Assignees: SmithKline Beecham p.l.c., United Kingdom; SmithKline Beecham Corporation

[21] Appl. No.: 08/940,730

[22] Filed: Sep. 30, 1997

Related U.S. Application Data

[60] Provisional application No. 60/027,223, Oct. 1, 1996, provisional application No. 60/027,222, Oct. 1, 1996, and provisional application No. 60/027,224, Oct. 1, 1996.

[30] Foreign Application Priority Data

Aug. 9, 1997 [GB] United Kingdom .................... 9716805
Sep. 11, 1997 [GB] United Kingdom .................... 9719203

[51] Int. Cl.⁶ ............................ A61K 31/35; A61K 9/06; A61K 9/10; A61K 9/107
[52] U.S. Cl. ............................ 514/460; 514/956; 424/434
[58] Field of Search ....................... 514/460, 956

[56] References Cited

U.S. PATENT DOCUMENTS

| | | | |
|---|---|---|---|
| 4,790,989 | 12/1988 | Hunter et al. | 424/704 |
| 4,879,287 | 11/1989 | Orr et al. | 514/171 |
| 4,916,155 | 4/1990 | Baker et al. | 514/468 |
| 5,594,026 | 1/1997 | Greenway et al. | 514/460 |

FOREIGN PATENT DOCUMENTS

| | | | |
|---|---|---|---|
| 0 069 423 | 1/1983 | European Pat. Off. | A61K 9/10 |
| 0 095 897 | 12/1983 | European Pat. Off. | A61K 9/06 |
| 0 167 856 | 1/1986 | European Pat. Off. | C07D 407/06 |
| 231621 | 8/1987 | European Pat. Off. | |
| 251434 | 1/1988 | European Pat. Off. | |
| WO 84/02076 | 6/1984 | WIPO | A61K 9/22 |
| WO 95/10999 | 4/1995 | WIPO | A61K 7/00 |
| WO9510999 | 4/1995 | WIPO | |
| WO9814189 | 4/1998 | WIPO | |

OTHER PUBLICATIONS

Bertino et al Am. J. Health–Syst. Pharm. 54(19): 2185–2191, 1997.
Naka Gawa et al Kagaku Ryohono Ryoiki 12(9): 1659–1667, 1995.
Anon: J. Am Soc. Nephrol. 7(11): 2403–2408, 1996.
Nakagawa et al Kagaku Ryohono Ryoiki 12(7): 1293–1296, 1996.
Finlay et al Antimicrob. Agents Chemotherapy 41(5): 1137–1139, 1997.
Nakamichi et al Yakurito Chiryo 24(1): 85–92, 1996.
Raz, Raul et al Arch Intern. Med. 156(10): 1109–1112, 1996.
Bloom et al Am. J. Kidney Dis. 27(5): 687–694, 1996.
Nsouli, et al., "Nasal Topical Antimicrobial Agent, Mupirocin–(Bactroban), in the Prophylaxis of Repeated Paranasal Sinusitis (RPS): A Double Blind Placebo Control Study", *Annals. of Allergy, Asthma and Immunology*, vol. 76(1): pp. 117, (1996).
"Mupirocin", *Merk Index*, 11th edn., pp. 993, (1989).

*Primary Examiner*—Shep Rose
*Attorney, Agent, or Firm*—Stephen Venetianer; Charles M. Kinzig; William T. King

[57] ABSTRACT

Mupirocin or a salt or ester thereof may be used to treat recurrent sinusitis and recurrent otitis, in particular with novel spray or cream formulations adapted for administration to the nasopharynx.

4 Claims, No Drawings

NASOPHARYNX ADMINISTRATION OF MUPIROCIN FOR PROPHYLACTIC TREATMENT OF RECURRENT OTITIS MEDIA

This application is based on Provisional Application Nos. 60/027,222, 60/027,223 and 60/027,224 all filed on Oct. 1, 1996.

The present invention relates to the use of mupirocin or a salt or ester thereof in treating certain bacterial infections, in particular recurrent otitis media and recurrent sinusitis, and to formulations for use in such treatment.

Mupirocin, formerly known as pseudomonic acid, is a therapeutically useful compound which exhibits good antibacterial activity, mainly against Gram-positive bacteria, but also against some Gram-negative bacteria such as *Haemophilus influenzae* and *Moraxella catarrhalis*. It acts as a selective reversible inhibitor of bacterial iso-leucyl t-RNA synthetase, thereby inhibiting bacterial protein synthesis (see Merck Index, 11th edn, 1989, 993 and references therein). The compound has an ester moiety which is susceptible to metabolism, effectively excluding the systemic use of the compound. It is however clinically effective as a topical agent.

Topical antibacterial compositions comprising mupirocin are marketed by SmithKline Beecham under the trade names Bactroban Ointment and Bactroban Nasal. The first product is an ointment comprising a water soluble polyethylene glycol base (see also EP 0 095 897-A, Beecham Group) whilst the second product comprises the calcium salt of mupirocin in a white soft paraffin based ointment containing a glycerin ester (see also EP 0 167 856-A, Beecham Group). More recently, topical creams comprising mupirocin or a salt thereof have been described (PCT/US94/12026, SmithKline Beecham). The formulation comprising the calcium salt of mupirocin in a white soft paraffin based ointment containing a glycerin ester (Bactroban Nasal) is particularly useful when applied to the anterior nares for the prophylactic eradication of the nasal carriage of *Staph aureus*. More recently, it has been found that the impact of such application is limited to the anterior nares. There is no significant reduction in the colonisation (by *H. influenzae, S. pneumonia* and *M. catarrhalis*) of the nasopharynx (unpublished).

A further potential therapeutic use of mupirocin has been described by Nsouli et al (poster presented at the Annual Meeting of the American College of Allergy, Asthma and Immunology, Nov. 10–15, 1995 and published in Annals of Allergy, Asthma and Immunology, January 1996, 76(1), 117). A spray formulation comprising Bactroban Ointment diluted in a 1:9 ratio with a saline solution (Ocean, Fleming & Co) was shown to be effective in reducing the incidence of recurrent paranasal sinusitis when administered twice daily (two 'puffs' of spray, estimated to be about 150–200 $\mu$l) over a seven month period. It is believed that efficacy of the mupirocin/saline combination is the result of erradication of nasal carriage of pathogenic bacteria associated with the recurrent episodes as the formulation would have no direct access to the sinus mucosa due to a small ostium which separates the nasopharynx from the maxillary sinuses. This dosage regimen may however not be ideal as there is concern that the use of a relatively low dosage over a prolonged period may encourage the development of mupirocin resistant bacteria. Furthermore, there may also be concerns about the desirability of the long term usage of aqueous solutions of mupirocin, given the known susceptibility of mupirocin to degradation in such an environment. There still remains the problem of providing a method of treatment for recurrent sinusitis which is devoid of the concerns mentioned above. In addition, there was no suggestion of other diseases which might be susceptible to similar treatment.

Otitis media is a disease state commonly seen in infants and young children. The acute condition is normally successfully treated with a systemic antibacterial agent such as amoxycillin, optionally in combination with potassium clavulanate. *H. influenzae, S. pneumonia* and *M. catarrhalis* are generally considered to be the most common bacterial pathogens. There however remains the problem of treating the recurrent painful episodes.

Accordingly, in a first aspect, the present invention provides for the use of mupirocin or a pharmaceutically acceptable ester or salt thereof in the manufacture of a medicament for the prophylactic treatment of bacterial infection associated with colonisation of the nasopharynx by pathogenic organisms, and in which the medicament is adapted for administration to, and residence within, the nasopharynx; excluding the use of a 0.2% saline solution of mupirocin for treating recurrent sinusitis, administered at a dosage of less than 1 mg a day, twice daily on a continuing basis.

Typical bacterial infections include recurrent otitis media and recurrent sinusitis.

Accordingly, in a further aspect, the present invention provides for the use of the use of mupirocin or a pharmaceutically acceptable ester or salt thereof in the manufacture of a medicament for the prophylactic treatment of recurrent otitis media.

In addition, the present invention also provides for the use of mupirocin or a pharmaceutically acceptable ester or salt thereof in the manufacture of a medicament for the prophylactic treatment of recurrent sinusitis.

As used herein, the term 'prophylactic treatment' includes not only complete elimination of the bacterial infection, for instance recurrent otitis media or recurrent sinusitis, but also a partial elimination of thereof, that is a reduction in the number of acute episodes.

It is believed that the successful treatment of bacterial infections, such as recurrent otitis media and recurrent sinusitis, is associated with the elimination or reduction of nasal carriage of pathogenic bacteria such as *S. aureus, H. influenzae, S. pneumonia* and *M catarrhalis*, in particular colonisation of the nasospharynx by such organisms.

Accordingly, in a further aspect, the present invention provides for the use of mupirocin or a pharmaceutically acceptable ester or salt in the manufacture of a medicament for reducing or eliminating the nasal carriage of pathogenic organisms associated with recurrent otitis media, which medicament is adapted for nasal administration, in particular, focussed delivery to the nasopharynx.

To lessen the risk of encouraging the development of mupirocin resistant organisms, it is preferred to administer of mupirocin or a pharmaceutically acceptable salt or ester thereof on an intermittent, rather than a continual, basis.

Accordingly, in a further aspect, the present invention provides the use of mupirocin or a pharmaceutically acceptable salt or ester thereof (hereinafter referred to as drug substance) in the manufacture of a medicament adapted for administration to the nasopharynx and which is administered to a patient in need thereof on an intermittent basis.

In a suitable intermittent treatment regimen, drug substance (mupirocin or a pharmaceutically acceptable ester or salt) is administered on a daily basis, for a small number of days, for instance from 2 to 10, suitably 3 to 8, more suitably about 5 days, the administration then being repeated after an interval, for instance, on a monthly basis over a period of months, for instance up to six months.

Less preferably, the drug substance may be administered on a continuing, daily basis, over a prolonged period, for instance several months.

Suitably drug substance is administered twice a day. Suitably, drug substance is administered during the winter months when bacterial infections such as recurrent otitis media and recurrent sinusitis tend to be more prevalent.

Suitably, drug substance is administered at a dosage of from 1 to 10 mg, preferably from 3 to 8, typically about 5 mg, in each nostril, twice a day.

The drug substance is administered to the nasopharynx, in particular the anterior nasopharynx.

Suitable pharmaceutically acceptable salts of mupirocin are well known in the art and include alkali metal salts such as sodium and lithium and alkaline earth metal salts such as calcium, of which the calcium salt is preferred, in particular the crystalline dihydrate form thereof described in EP 0 167 856-A (Beecham Group), as well as other metal salts, for instance silver and aluminiun salts and ammonium substituted ammonium salts. The salts may be anhydrous or may be in the form of pharmaceutically acceptable solvates, for instance alcoholates and, especially, hydrates. Preferred salts include the calcium, silver and lithium salts, in particular the calcium salt. In the case of the calcium salt of mupirocin, the crystalline salt, preferably the crystalline hydrated calcium salt, more preferably the crystalline dihydrate salt, is used. Preferably, the crystalline hydrated calcium salt is used.

Accordingly, in a further aspect, the present invention provides for the use of the crystalline calcium dihydrate salt of mupirocin in the manufacture of a medicament for the prophylactic treatment of conditions associated with bacterial colonisation of the nasopharynx.

Suitable pharmaceutically acceptable esters are well known in the art and include lower alkyl esters, especially the methyl and ethyl esters.

Suitably, the drug substance is present in medicaments for use in the present invention inn between 0.01 and 10%, preferably 0.1 and 5%, more preferably 1 and 5%. Suitable amounts include 2% and 4% by weight of the medicament. It is preferred to avoid low level dosages of drug substance as this might increase the risk of the development of mupirocin resistant bacteria.

Accordingly, in a further aspect, the present invention provides for the use of mupirocin or a pharmaceutically acceptable salt or ester thereof in the manufacture of a medicament for the prophylactic treatment of bacterial infection, characterised in that the medicament is administered to the nasopharynx and comprises from 0.5 to 5% by weight of mupirocin or a pharmaceutically acceptable salt or ester.

Preferred compositions for administration include those adapted for focussed delivery to, and residence within, the nasopharynx. The term 'focussed delivery' is used to mean that the composition is delivered to the nasopharynx, rather than remaining within the nares. The term 'residence' within the nasopharynx is used to mean that the composition once delivered remains within the nasopharynx over a course of several hours, rather than being washed away more or less immediately. These two aspects may be conveniently studied by γ (gamma) ray scintigraphy. Suitable such compositions include sprays and creams.

Accordingly, in a further aspect, the present invention provides for a sprayable pharmaceutical formulation comprising:

(a) an amphiphilic agent that increases in viscosity on contact with water;

(b) a non-aqueous diluent for the amphiphilic agent, (c) powdered drug substance in suspension.

Amphiphilic agents are substances containing both hydrophilic and lipophilic groups. In liquid form, these agents are generally capable of spontaneous self-association in the presence of water, with a consequent increase in viscosity. This self-association results in a change in properties ranging from the formation of viscous liquids to semi-rigid gels. This behaviour has been characterised as due to the formation of long range order in the liquid system giving several distinct phases which have been called "liquid crystalline phases".

Materials known to exhibit such properties and which are suitable for use in a pharmaceutical formulation include mono-glycerides such as mono-olein and mono-linolein, phospholipids such as phosphatidyl cholines, and galacto-lipids such as galactoyldiglycerides.

Typically the monoglyceridies are long-chain fatty acid monoglycerides, optionally comprising up to 10% (w/w) of a long-chain fatty acid diglyceride and/or a small amount by weight of a free long-chain fatty acid. The mono- and di-glycerides may each include blends of different long-chain fatty acid mono- and di-glycerides. Suitable long-chain fatty acid monoglycerides include glycerol monooleate, glycerol monopalmitate and glycerol mono stearate. Suitable commercially available examples of such include the products available under the trade names MYVEROL, such as MYVEROL 18–99, MYVATEX, MYVAPLEX, and GMORPHIC 80 respectively, from Eastman Kodak Chemicals, Rochester, N.Y. A further useful long-chain fatty acid monoglyceride-containing product is ARLACEL 186 (available from ICI Americas Inc.) which includes, in addition to glycerol monooleate, propylene glycol (10%). The main fatty acids of MYVEROL 18–99 are oleic acid (61%), linoleic acid (21%), linolenic acid (9%) and palmitic acid (4%). Suitably in such long-chain monoglycerides, the major fatty acid component is a $C_{18}$-saturated, monounsaturated or polyunsaturated fatty acid, preferably a $C_{18}$-monounsaturated or polyunsaturated fatty acid. Suitably the monoglyceride will have an HLB value in the range of about 2.5 to 6. The HLB value of the product MYVEROL 18–99 is 3.7.

In the present invention the amphiphilic substance is preferably glyceryl mono-oleate (mono-olein). As indicated above, in its commercially available form, glyceryl mono-oleate is a material which is predominantly glyceryl mono-oleate but also contains minor amounts of related mono and di-glycerides. Accordingly, the amount that is effective in a particular spray formulation will vary dependent on the level of glyceryl mono-oleate in the commercial material used.

To obtain a sprayable formulation, the amphiphilic substance is combined with a liquid diluent. The diluent is selected on the basis of compatibility e.g. producing a stable blend with the amphiphilic agent, and the ability to achieve a sprayable blend without excessive dilution that will reduce the self-association on contact with water and detract from the desired viscosity increase. Typically, a diluent is a pharmaceutically acceptable oil, most preferably a fatty acid triglyceride, typically vegetable (i.e. plant derived) oil, since mineral oils such as paraffin oil have been implicated in undesirable side effects when inhaled. Suitable vegetable oils include coconut oil, sesame oil and soya bean oil. In this invention, the preferred diluent is a vegetable oil, most preferably coconut oil, that has been fractionated so that it is predominantly medium chain length triglycerides. Typically the proportion of amphiphilic agent to oil is from 2:1 to 1:4, preferably 1:1 to 1:2. Ideally, the amount of diluent is adjusted so that the formulation is of a viscosity that is suitable for spray delivery at 20° C. or above.

Suitable medium-chain fatty acid triglycerides for use in the present invention may be of natural, semi-synthetic or synthetic origin and may include blends of different medium chain fatty acid triglycerides. The term "medium-chain fatty acid" as used herein refers to a fatty acid having from 6 to 12, preferably 8 to 10 carbon atoms which may be branched or unbranched, preferably unbranched and which may be optionally substituted. Certain neutral plant oils, such as fractionated coconut oils, provide convenient sources of medium-chain fatty acid triglycerides. The triglyceride suitably comprises from 50 to 100% (w/w) of caprylic ($C_8$) acid and from 0 to 50% (w/w) of capric ($C_{10}$) acid triglycerides. Suitable examples include those available under the trade names MYRITOL; CAPTEX (Karlshams Lipid Specialties, Columbus Ohio), for instance CAPTEX 355, CAPTEX 300, CAPTEX 350, CAPTEX 850 and CAPTEX 8000; MIGLYOL (BASF), for instance the grades MIGLYOL 810, MIGLYOL 812 AND MIGLYOL 818 (which also comprises a linoleic acid triglyceride) and MAZOL 1400 (Mazer Chemical, Guernee, Ill.). The fatty acid content of representative products is: CAPTEX 355™—CAPROIC ACID (2%), CAPRYLIC ACID (55%) and capric acid (42%); CAPTEX 8000—at least 98% caprylic acid, MYGOL 810—caproic acid (2%), caprylic acid (65–75%), capric acid (25–35%) and MIGLYOL 812—caproic acid (3%), caprylic acid (50–65%), capric acid (30–45%) and lauric acid (5%) (manufacturer's data).

In the present formulations, the drug substance is used at between 2 and 8%, suitably between 3 and 5%, typically about 4%, by weight of the formulation. It is preferred to use a relatively high dosage level, to reduce the risk of the development of bacterial resistance. Also, to avoid excessive delivery volumes which will be uncomfortable in nasal administration, the drug substance is preferably present at a relatively high loading compared to other topical administration formulations.

Suitably, the drug substance is micronised calcium mupirocin dihydrate. Suitably the drug substance has a particle size less than 100 μm, preferably less than 10 μm.

The sprayable formulations of this invention are especially suitable for delivery to and residence within the nasopharynx, because in the humid environment of the nasal passages they increase in viscosity by contact with water, and so are better able to resist wash-out when in contact with nasal surfaces.

Other sprayable formulations for use in the present invention include solutions of drug substance, preferably mupirocin, in aqueous polyethylene glycol. Such sprays may be conveniently prepared on an extemporaneous basis by diluting a pharmaceutical composition comprising drug substance, preferably mupirocin, in polyethylene glycol, or a derivative thereof, with an aqueous solution, for instance water, or, preferably, a saline solution. Suitable such compositions are described in EP 0 095 897-A2 (Beecham Group). Suitably, the pharmaceutical composition comprises from 0.01 to 50% mupirocin in polyethylene glycol, suitably a mixture of polyethylene glycol 400 and polyethylene glycol 4000. In a representative example, the pharmaceutical composition comprises 2% mupirocin in mixture of polyethylene glycol 400 (59%) and polyethylene glycol 4000 (39%). Suitably, the mupirocin containing composition is diluted with aqueous solution in a ratio of from 1:1 to 1:20, more suitably 1:5 to 1:15, preferably about 1:9 to 1:10. Suitably, in the nasal spray, drug substance is incorporated at between 0.01 and 1%, suitably 0.1 to 0.5% by weight of the composition. Suitably such aqueous compositions comprising mupirocin are stored at about 5° C. and are not stored for prolonged periods, as mupirocin is known to be susceptible to degradation on prolonged exposure to an aqueous environment.

The mupirocin formulation and aqueous solution for the extemporaneous preparation of the nasal spray may be conveniently provided in a kit. Accordingly, in a further aspect, the present invention provides for a kit comprising, in a first part, a pharmaceutical formulation comprising drug substance, preferably mupirocin, in polyethylene glycol, or a derivative thereof, as hereinbefore described, and, in a second part, an aqueous solution. The first and second parts may be supplied in separate containers or in single container with the two parts separated by a barrier which is removed or broken prior to use. Suitably the kit includes a container adapted for use as a nasal spray device.

Further suitable formulations include creams adapted for focussed delivery to the nasopharynx. Such formulations with appropriate viscosity characteristics may be provided in containers adapted for nasal administration, for instance having an extended nozzle.

According, in a further aspect, the present invention provides a pharmaceutical formulation consisting essentially of 2–8% by wt. of drug substance;

50–70% by wt. of a fatty acid triglyceride;

2–6% by wt. of a polyoxyethylene ether or ester surfactant;

2–4% by wt. of a fatty alcohol or ester;

30–40% by wt. of water; and up to 2% by wt. of conventional additive such as preservatives and flavourings.

For nasal administration the issue of patient comfort is important in compliance with the intended treatment regime. The formulation of this invention provides a low viscosity cream that is easy to administer and which readily changes in consistency and softens in the temperature conditions of the nose. Accordingly when inserted into the upper regions of the nose it can be transported deeper into the nasal passages by natural processes. The composition is intended to be in the form of an oil-in-water cream emulsion. In view of the large triglyceride content which provides the desired consistency for nasal administration, and the relatively low content of surfactant, the amounts of the components within the above ranges must be selected for individual components by routine trials to ensure that an oil-in-water emulsion is obtained.

The fatty acid triglycerides are typically vegetable (i.e. plant-derived) oils, such as coconut oil, sesame oil or soya bean oil. An especially suitable vegetable oil is one that has to been fractionated so that it is predominantly medium chain length triglycerides.

Suitable medium-chain fatty acid triglycerides for use in the present invention may be of natural, semi-synthetic or synthetic origin and may include blends of different medium chain fatty acid triglycerides. The term "medium-chain fatty acid" as used herein refers to a fatty acid having from 6 to 12, preferably 8 to 10 carbon atoms which may be branched or unbranched, preferably unbranched and which may be optionally substituted. Certain neutral plant oils, such as fractionated coconut oils, provide convenient sources of medium-chain fatty acid triglycerides. The triglyceride suitably comprises from 50 to 100% (w/w) of caprylic ($C_8$) acid and from 0 to 50% (w/w) of capric ($C_{10}$) acid triglycerides. Suitable examples include those available under the trade names MYRITOL; CAPTEX (Karlshams Lipid Specialties, Columbus Ohio), for instance CAPTEX 355, CAPTEX 300, CAPTEX 350, CAPTEX 850 and CAPTEX 8000; MIGLYOL (BASF), for instance the grades MIGLYOL 810, MIGLYOL 812 AND MIGLYOL 818 (which also comprises a linoleic acid triglyceride) and MAZOL 1400 (Mazer Chemical, Guernee, Ill.). The fatty acid content of representative products is: CAPTEX 355™—CAPROIC ACID (2%), CAPRYLIC ACID (55%) and capric acid (42%); CAPTEX 8000—at least 98% caprylic acid, MYGOL 810— caproic acid (2%), caprylic acid (65–75%), capric acid (25–35%) and MIGLYOL 812—caproic acid (3%), caprylic acid (50–65%), capric acid (30–45%) and lauric acid (5%) (manufacturer's data).

The polyoxyethylene ether or ester used in this invention is one which will function as a non-ionic surfactant. Especially suitable materials include polyoxyethylene glycol monocetyl ethers, such as Cetomacrogol 1000. Other suitable non-ionic surfactants include:

(a) polyoxyethylene fatty acid esters, for example polyoxyethylene stearic acid esters of the type available under the trade name MYRJ (ICI Americas, Inc.), for instance the product MYRJ 52 (a polyoxyethylene 40 stearate);

(b) polyoxyethylene-sorbitan fatty acid esters (polysorbates), for example the mono- and tri-lauryl, palmityl, stearyl and oleyl esters, for instance the polyoxyethylene sorbitan monooleates available under the trade name of TWEEN (ICI Americas Inc.), such as TWEEN 20, 21, 40, 60, 61, 65, 80, 81 and 85, of which class TWEEN 80 is especially preferred;

(c) polyoxyethylene glycol long-chain alkyl ethers, such as polyoxyethylated glycol lauryl ether; and (d) polyoxyethylene glycol long-chain alkyl esters, such as PEG-monostearate.

For use herein, the surfactant preferably has an HLB value in the range of 13 to 20.

As fatty alcohol or ester there may be used any of such materials conventionally used in pharmaceutical or veterinary formulations such as stearyl alcohol, cetyl alcohol, cetyl stearyl alcohol, myristyl alcohol and glycerin monostearate. Preferably, cetostearyl alcohol is used, or a mixture of stearyl alcohol and cetyl alcohol.

A particularly preferred vehicle formulation comprises fractionated coconut oil (typically about 55 to 60, especially about 57, parts by weight); polyoxyethylene glycol monocetyl ether (typically about 2 to 4, especially about 3, parts by weight); cetostearyl alcohol (typically about 2 to 4, especially about 3, parts by weight); with water for emulsification, and also preservatives, and flavourings if desired.

Typical preservatives include benzyl alcohol and phenoxyethanol.

Suitably, the drug substance is the calcium salt of mupirocin, in particular the calcium dihydrate salt. This is preferably present as a finely divided powder. This may be achieved by milling, and most suitably by micronising (fluid energy milling) so that the medicament has a particle size less than 100 $\mu$m, preferably less than 10 $\mu$m.

In the formulation of this invention the drug substance is used at between 2 and 8%, suitably between 3 and 5%, typically about 4%, by weight of the formulation. It is preferred to use a relatively high dosage level, to reduce the risk of the development of bacterial resistance. Also, to avoid excessive delivery volumes which will be uncomfortable in nasal administration, the drug substance is preferably present at a relatively high loading compared to other topical administration formulations.

The formulation may typically be administered into the nasal passages by a pump, such as an air lift pump. This may be adapted for nasal administration by addition of a modified nozzle.

Formulations of this invention may be produced by conventional pharmaceutical techniques. Thus, for example, the components of the carrier may be blended by mixing together at an elevated temperature until an emulsion has formed. The mixture may then be cooled to room temperature, and, after the addition of any further optional ingredients, stirred to ensure adequate dispersion. The antibiotic may be added during hot preparation of the base, or may be added with additional ingredients after cooling of the base. If necessary the composition may be provided in sterile condition.

Optional ingredients that may be added if desired include colourings and flavourings.

The skilled person will readily appreciate that in the novel spray and cream formulations hereinbefore described, mupirocin may be replaced by another antibiotic agent. The present invention encompasses all such formulations.

The invention is illustrated by the following Examples.

EXAMPLE 1

Spray Formulation

A carrier for a nasal spray formulation was prepared by forming a blend of 67% w/w fractionated coconut oil (medium chain length)* and 33% w/w of glyceryl monooleate

**. To this blend was added 0.2% w/w of powdered lemon juice flavour, followed by 4% w/w of micronized calcium Mupirocin.

The resultant formulation has a viscosity which is sprayable at 20° C. or above. When sprayed into the nose of a patient, the liquid coats the nasal passages and contact with moisture inside the nose (from the mucous membranes, and the humid environment generally) causes the carrier to thicken. This prolongs the residence time of the sprayed formulation on the nasal surfaces. A spray volume of about 125 $\mu$l contains approximately 5 mg Mupirocin.

*Commercial product Miglyol, obtainable from Hüls
** Commercial product Myverol 18–99, obtainable from Eastman

EXAMPLE 2

Cream

An oil-in-water emulsion cream was prepared from the following:

| | |
|---|---|
| Calcium Mupirocin | 4% |
| Fractionated Coconut Oil* | 57.3% |
| Polyoxyethylene glycol monocetyl ether | 3% |
| Cetostearyl alcohol | 3% |
| Benzyl Alcohol | 1% |
| Phenoxy ethanol | 0.5% |
| Water | 35% |
| Lemon juice flavour (powdered) | 0.2% |

*Commercial product Miglyol, obtainable from BASF

I claim:

1. A method for the prophylactic treatment of recurrent otitis media which method comprises administering an effective amount of mupirocin of a pharmaceutically acceptable ester of salt thereof adapted for administration to, and residence within, the nasopharynx, to a patient in need thereof.

2. The method as claimed in claim 1 in which the medicament is administered on a the nasopharynx of a patient in need thereof on an intermittent basis.

3. The method as claimed in claim 2 in which the medicament is administered on a daily basis, for 2 to 10 days, and then repeated on a monthly basis.

4. The method as claimed in claim 1 in which mupirocin or a pharmaceutically acceptable ester or salt thereof is administered at a dosage of from 1 to 10 mg in each nostril, twice a day.

* * * * *